United States Patent [19]
Kaplan

[11] 4,201,786
[45] May 6, 1980

[54] WATER SOLUBLE PESTICIDAL QUATERNARY AMMONIUM SALT COMPOUNDS

[75] Inventor: Barbara W. Kaplan, Charleston, W. Va.

[73] Assignee: Union Carbide Corporation, New York, N.Y.

[21] Appl. No.: 801,333

[22] Filed: May 27, 1977

[51] Int. Cl.[2] .................... A61K 31/36; A61K 31/34; C07D 317/44; C07D 307/78

[52] U.S. Cl. .............................. 424/282; 260/307 G; 260/326.35; 260/326.36; 260/340.3; 260/340.5 R; 260/346.73; 424/248.54; 424/263; 424/273; 424/274; 424/275; 424/285; 544/153; 544/238; 544/333; 544/336; 546/171; 546/175; 546/196; 546/197; 546/269; 546/270; 548/336; 548/131; 548/236; 549/51

[58] Field of Search ..................... 260/346.22, 346.73; 424/285, 275

[56] References Cited

U.S. PATENT DOCUMENTS

| | | | |
|---|---|---|---|
| 3,404,208 | 10/1968 | Robertson et al. | 424/300 |
| 3,474,170 | 10/1969 | Scharpf | 424/285 |
| 3,547,955 | 12/1970 | Scharpf | 260/346.22 |
| 3,819,683 | 6/1974 | Krebs et al. | 260/346.22 X |
| 4,027,033 | 5/1977 | Chodnekar et al. | 424/282 |
| 4,032,649 | 6/1977 | Singerman | 424/275 |
| 4,064,250 | 12/1977 | Gates | 424/282 |

FOREIGN PATENT DOCUMENTS

| | | | |
|---|---|---|---|
| 1107411 | 3/1968 | United Kingdom . | |
| 1160977 | 8/1969 | United Kingdom | 260/346.22 |

*Primary Examiner*—Ethel G. Love
*Attorney, Agent, or Firm*—Clement J. Vicari

[57] ABSTRACT

Water soluble quaternary ammonium salt compounds exhibit outstanding insecticidal and miticidal activity coupled with reduced mammalian toxicity and acceptable phytotoxicity.

48 Claims, No Drawings

WATER SOLUBLE PESTICIDAL QUATERNARY AMMONIUM SALT COMPOUNDS

This invention relates to N-alkyl-N-alkanoyl aryl carbamate salt compounds which contain a quaternary nitrogen moiety and to their preparation. This invention is also directed to insecticidal and miticidal compositions comprising an acceptable carrier and as the active toxicant an insecticidally or miticidally effective amount of a compound of this invention, as well as to a method of controlling insects and mites by subjecting them to an insecticidally or miticidally effective amount of a compound of this invention.

More particularly, this invention relates to compounds of the formula:

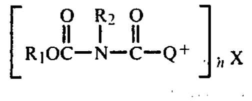

wherein:

n is 1, 2 or 3;

$R_1$ is benzofuranyl, benzodioxanyl, benzothienyl, dihydrobenzothienyl, benzodioxolanyl or dihydrobenzofuranyl all of which may be either unsubstituted or substituted with one or more alkyl groups having from 1 to 8 carbon atoms;

$R_2$ is alkyl having from 1 to 8 carbon atoms;

X is a monovalent, divalent or trivalent inorganic or organic anion whose total charge equals n;

As indicated above, X may be any monovalent, divalent or trivalent inorganic or organic anion. Illustrative of the wide range of permissible X groups are:

Monovalent inorganic anions, such as chloride, bromide, fluoride, nitrate, iodide and bicarbonate;

Divalent inorganic anions, such as carbonate and sulfate;

Trivalent inorganic anions such as phosphate;

Monovalent organic anions such as acetate propionate, lactate and formate;

Divalent organic anions such as succinate, maleate and tartrate.

Trivalent organic anions such as citrate;

Arenesulfonates such as p-toluenesulfonate and benzenesulfonate;

Alkanesulfonates such as methanesulfonate and ethanesulfonate.

Examples of radicals which $R_1$ may represent are 2,3-dihydro-2,2-dimethyl benzofuranyl, 2,3-dihydro-2-methylbenzofuranyl and 2,2-dimethyl-1,3-benzodioxolanyl.

The alkyl groups which $R_2$ may represent include methyl, ethyl, isopropyl, n-propyl, hexyl, octyl, isobutyl and the like.

In the preferred embodiments of this invention, $Q^+$ is an organic radical of the formula:

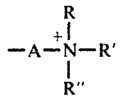

wherein:

A is a divalent aliphatic hydrocarbon having from 1 to 25 carbon atoms. R, R′ and R″ are:

(A) individually either substituted or unsubstituted alkyl, alkoxyalkyl, alkenyl or alkynyl; or (B) When R and R′ are the same or different and are methyl or ethyl, R″ is either a substituted or unsubstituted phenyl, naphthyl, cycloalkyl, cycloalkenyl or either a 5 or 6 membered ring structure which may include one or two heteroatoms of oxygen and/or nitrogen; or (C) when R is alkyl of from 1 to 4 carbon atoms, R′ and R″ together may form either a substituted or unsubstituted alkenylene or alkylene chain having from 2 to 20 carbon atoms, which completes a 3, 4, 5, 6, 7, 8 or 9 membered monocyclic ring structure, said chain may include one or two heteroatoms of oxygen and/or nitrogen; or (D) R, R′ and R″ together may form either a substituted or unsubstituted alkylene or alkenylene chain having from 2 to 20 carbon atoms which completes a 3, 4, 5, 6, 7, 8 or 9 membered monocyclic or bicyclic ring structure, said chain may include one or two heteroatoms of oxygen and/or nitrogen;

wherein the permissible substituents that may be substituted on R, R′ and R″ are one or more alkyl alkoxy, alkanoyloxy, alkoxycarbonyl, cyano, halo, nitro, dialkylamino or alkanoyl groups;

with the proviso that the sum of aliphatic carbon atoms included in R, R′ and R″ may not be more than thirty five.

Examples of specific radicals which $Q^+$ may represent are:

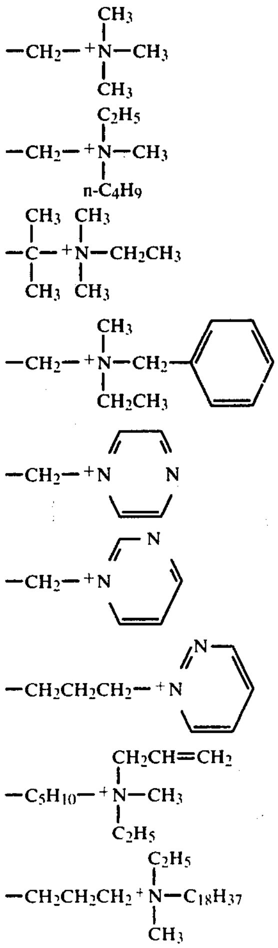

-continued
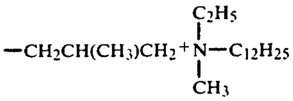
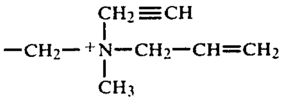
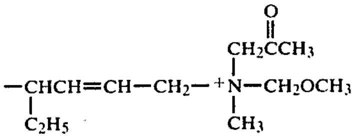
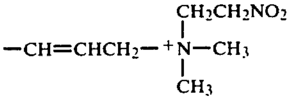
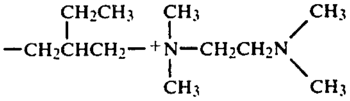
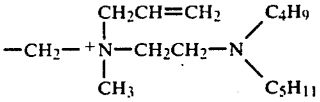
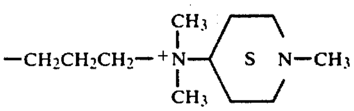
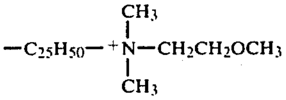
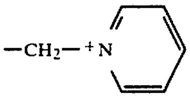
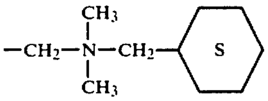
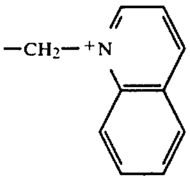
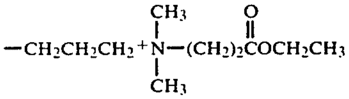
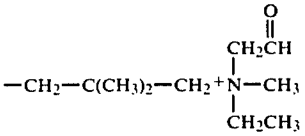
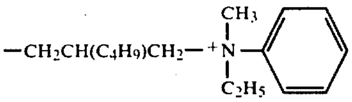
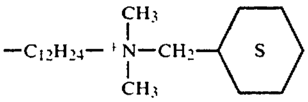
-continued
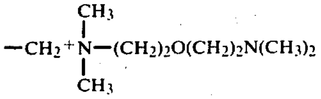
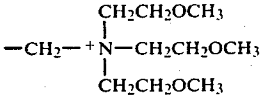
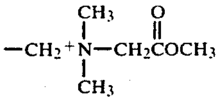
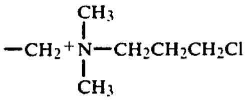
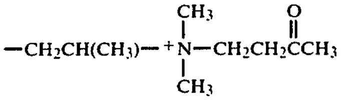
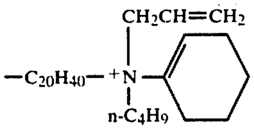
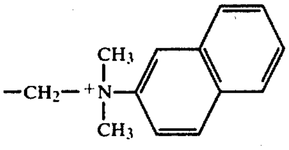
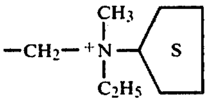
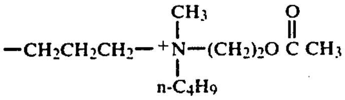
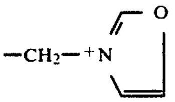
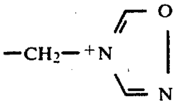
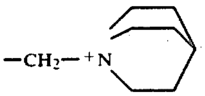
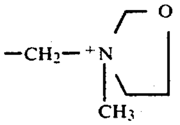
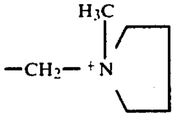
The following compounds are illustrative of the compounds of this invention:

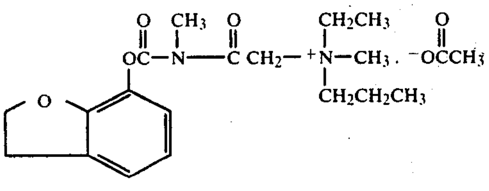

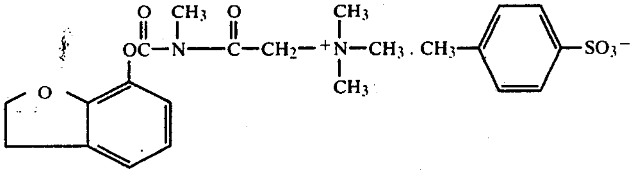

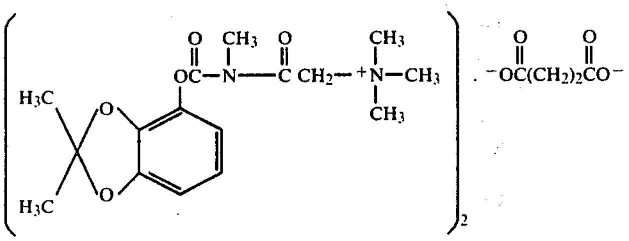

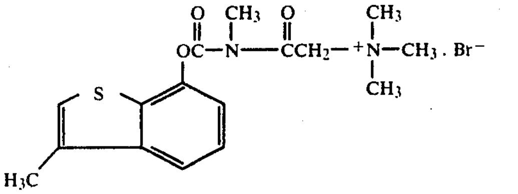

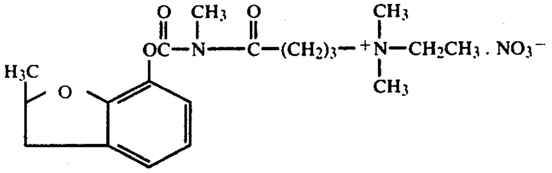

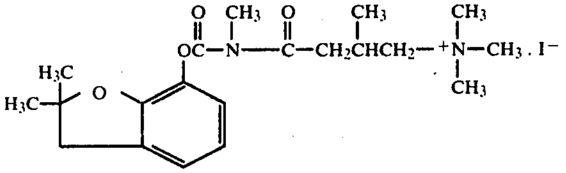

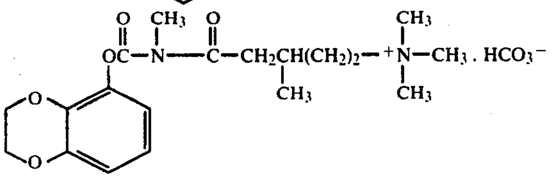

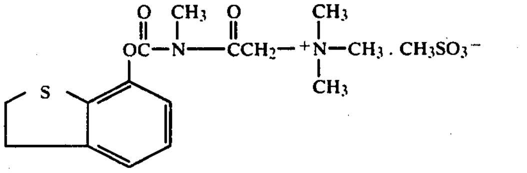

All of the compounds within the purview of the generic formula set forth above exhibit nematocidal, miticidal and insecticidal activity to a lesser or greater extent. Accordingly, these compounds are extremely useful for the control of insect, nematode and mite pests. Some of these compounds exhibit very high levels of miticidal, nematocidal and insecticidal activity in extremely small dosages while others require larger do dosages to be effective. These compounds also exhibit substantially reduced levels of peroral mammalian toxicity as compared to known pesticidal compounds having a comparable spectrum of activity against insect, mite and nematode pests.

The compounds of this invention also exhibit relatively high levels of water solubility as compared to known pesticidally active compounds exhibiting comparable levels of activity. The increased water solubility facilitates the application of the active compounds to the pest. For example, the compounds of this invention which are water soluble can be conveniently and easily used for pest control merely by dissolving the compound directly into water, and then applying the aqueous solution to the pest by some appropriate method, such as spraying. This avoids many of the problems associated with formulations such as crystallization, layer separation, aglomeration and the like.

Preferred, because of their higher levels of insecticidal, nematocidal and miticidal activity and because of their significantly reduced levels of peroral mammalian toxicity and acceptable crop plant phytotoxicity are the compounds of this invention in which:

X is chloride, bromide, nitrate, formate, acetate, p-toluenesulfonate, sulfate, carbonate, methanesulfonate, trifluoromethanesulfonate, phosphate, citrate, propionate, palmitate, laurate, glutarate or valerate.

$R_1$ is dihydrobenzofuranyl or benzodioxalanyl either unsubstituted or substituted with one or more alkyl substituents having from one to four carbon atoms;

$R_2$ is methyl;

A is a divalent aliphatic hydrocarbon having from 1 to 25 carbon atoms; and

R, R' and R" are as described hereinabove.

The compounds of this invention can be prepared by a variety of methods. One preferred method is illustrated by the general reaction scheme set forth below in which $R_1$, $R_2$, R, R', and R" are as described above and X is halide, arenesulfonate or alkanesulfonate except as noted:

METHOD I

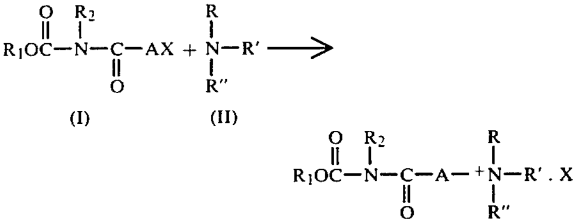

(I) (II) (III)

In Method I, X is preferably chloride, bromide alkanesulfonate or arenesulfonate.

The reaction illustrated in Method I is carried out by contacting an equivalent of the intermediate (I) with at least one equivalent of the tertiary amine (II) reactant in either an excess of the tertiary amine (II) reactant or in an appropriate solvent. In general, any organic solvent which is relatively inert to the reactants under the reaction conditions may be employed. Illustrative of the organic solvents which are useful as reaction solvents are saturated and unsaturated aliphatic and aromatic hydrocarbons, e.g. petroleum ether, hexane, cyclohexane, octane, dodecane, naphtha, decalin, kerosene, tetrahydronaphthalene, cycloheptane, methylcyclohexane, benzene, toluene, xylene, naphthalene, ethylbenzene, methylnaphthalene, or the like; ethers such as tetrahydrofuran, tetrahydropyran, diethyl ether, dioxane, 1,2-dimethoxybenzene, 1,2-ethoxybenzene, and dialkyl ethers of ethylene glycol, of diethyleneglycol of triethylene glycol, of dipropylene glycol, of butylene glycol, of diethylene glycol, of dipropylene glycol; chlorinated aliphatic hydrocarbons as for example, chloroform, dichloromethane, 1,1-dichloroethane, carbon tetrachloride; ketones, such as acetone or methyl ethyl ketone; and esters such as ethyl acetate.

In general, reaction pressures are not critical. The reaction can be conveniently conducted at either subatmospheric, atomospheric or superatmospheric pressure.

The reaction temperature is not critical and can be varied over a wide range. The process normally can be conducted at a temperature in the range of from about −30° C. and upwards to approximately 180° C. Preferred reaction temperatures are from about 0° C. to about 130° C. At temperatures below −30° C. the rate of reaction because markedly slower, while a temperatures above 180° C. product degradation may occur.

Compounds of this invention wherein X is other than halide, alkanesulfonate or arenesulfonate may be conveniently prepared by treating the corresponding quaternary monium halide salt compound with the acid of the desired anion or alternatively by passing the solution of the corresponding quaterary ammonium chloride salt in water or an organic solvent through an ion exchange resin charged with the appropriate anion. For example, 2,3-dihydro-2,2-dimethyl-7-benzofuranyl N-(dimethylaminoacetyl)-N-methyl carbamate methonitrate can be conveniently prepared by treating 2,3-dihydro-2,2-dimethyl-7-benzofuranyl N-(dimethylaminoacetyl)-N-methylcarbamate methochloride with a molar excess of nitric acid in distilled water. By way of a specific illustration of the ion exchange resin method, 2,3-dihydro-2,2-dimethyl-7-benzofuranyl N-(dimethylaminoacetyl)-N-methylcarbamate methoacetate can be conveniently prepared by passing a solution of 2,3-dihydro-2,2-dimethyl-7-benzofuranyl N-(dimethylaminoacetyl)-N-methylcarbamate methochloride in an unreactive solvent, such as water or methylene chloride, through the acetate form of an appropriate resin, as for example, a poly-styrene type polymer containing quaternary ammonium acetate groups.

The amine compounds utilized as reactants in the reaction of Method I are well known compounds that can be either obtained from commercial sources or prepared in accordance with methods well known to those skilled in the synthetic art.

The N-haloalkanoyl -N-alkyl aryl carbamate compounds utilized as reactants in the reaction of Method I can be prepared in accordance with a variety of conventional methods. Three useful methods are illustrated by the reaction schemes set forth below in which $R_1$, $R_2$ and A are as described above and X is chloride and X' is chloride or fluoride and U is iodide, alkanesulfonate arenesulfonate, chloride or bromide.

METHOD II

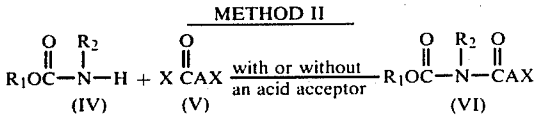

(IV) (V) (VI)

METHOD III

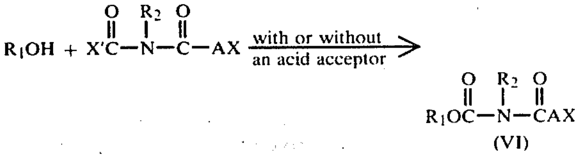

(VI)

METHOD IV

A.

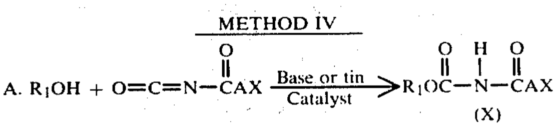

(X)

B.

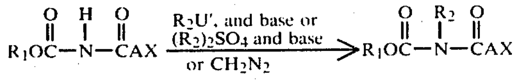

In Method IV, $R_2$ is alkyl.

The reactions illustrated in Methods II, III and IV, can be conveniently carried out by contacting equivalent amounts of the reactants and reagents in a suitable nonreactive solvent such as toluene, benzene, methylene chloride, tetrahydrofuran or the like.

Illustrative of useful bases and acid acceptors are tertiary amines, sodium bicarbonate, sodium hydroxide, sodium carbonate, potassium hydroxide and the like. Reaction temperatures and pressures are not critical. The reactions can be conducted over a broad temperature and pressure range to yield the desired products.

Intermediates (I) of METHOD I in which X is other than chloride, e.g. p-toluenesulfonate, may be conveniently prepared by treating the corresponding chloride compound with salt of the appropriate X group, as for example, sodium p-toluenesulfonate in an appropriate solvent, such as methylene chloride. Such substitutions are well known to those skilled in the art.

The N-alkyl arylcarbamate reactant (IV) of Method II can be either obtained from commercial sources or conveniently prepared by reacting an appropriately substituted isocyanate with the corresponding hydroxyl aryl compound in the presence of a catalyst, such as a tertiary amine or a tin compound. The haloalkanoyl halide (V) reactant of METHOD II is a well known compound which can be obtained from commercial sources or prepared by known procedures.

The haloalkanoyl isocyanate IX reactant of METHOD IV is a known compound which can be conveniently prepared by the method disclosed in A. J. Speziale and L. R. Smith, J. Org. Chem., 27, 3742 (1963); 28, 1805 (1963).

The following specific examples are presented to more particularly illustrate the manner in which the compounds of this invention can be prepared.

EXAMPLE I

The preparation of a compound of the formula:

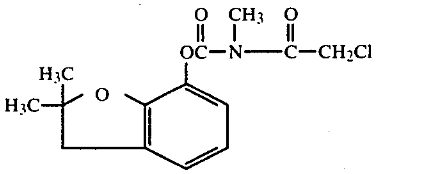

2,3-Dihydro-2,2-dimethyl-7-benzofuranyl N-methylcarbamate (15 g, 0.068 moles) and an excess of chloroacetyl chloride were stirred in refluxing xylene until nuclear magnetic resonance spectroscopy (NMR) showed the reaction to be nearly complete. Partial evaporations and additions of petroleum ether resulted in the crystallization of unreacted starting material, which was removed by filtration. The residue was concentrated to yield 14.54 g. (72%) of the compound structurally depicted above as an oil.

Anal. Calc'd for $C_{14}H_{16}ClNO_4$: C, 56.48; H, 5.42; N, 4.70. Found: C, 57.16; H, 5.50; N, 4.46.

NMR ($CDCl_3$+TMS): $\delta$=7.26–6.6 (3H); 4.75 (2H); 3.37 (3H); 3.09 (2H); 1.49 (6H).

EXAMPLE II

The preparation of the compound of the formula:

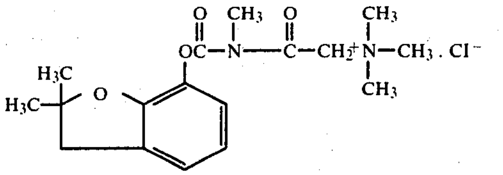

Trimethylamine (200 ml) was addes to 390 g (1.31 m) of crude 2,3-dihydro-2,2-dimethyl-7-benzofuranyl N-chloroacetyl-N-methylcarbamate and 1 liter of benzene in a 5 liter 4-neck round-bottom flask fitted with theremomether, air-stirrer, addition funnel, and dewar condenser cooled with dry-ice/acetone under a nitrogen flow-system. An additional 800 ml of benzene were added because the large amounts of solids out of solution resulted in inefficient stirring. After stirring overnight (16 hours) one liter of benzene was added and the mixture was filtered. The reaction product was collected by filtration then dissolved in $CH_2Cl_2$. The mixture was then treated with charcoal, filtered through celite, and partially evaporated. The reaction product which crystallized out was collected by filtration and washed with benzene and hexane, and then recrystallized from $CH_2Cl_2$-hexane mixture. The reaction product was then recrystallized again from a $CH_2Cl_2$-hexane mixture and washed well with hexane to yield 239 g of the compound structurally depicted above crystals, mp 179° sharp, which contained 1 mole of water per mole of the compound.

Anal. Calc. for $C_{17}H_{25}C_1N_2O_4$: C, 57.22; H, 7.06; N, 7.85. Calc. for $C_{17}H_{25}C_1N_2O_4.H_2O$; C, 54.1; H, 7.2; N, 7.5. Found: C, 54.44; H 7.11, N, 7.47.

NMR($CDCl_3$+TMS): $\delta$=7.3–68 (3H); 5.5-5.0(2H); 3.9-2.8 (3 distinct broad absorptions 16H); 1.49 (6H).

EXAMPLE III

The Preparation of the compound of the formula:

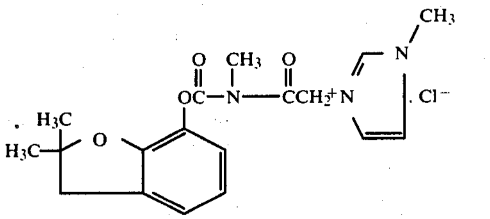

2,3-Dihydro-2,2-dimethyl-7-benzofuranyl N-chloroacetyl-N-methylcarbamate (3.0 g 0.010 m) and N-methylimidazole (1.0 g, 0.011 m) were stirred in 12 ml of benzene for 1.5 hours at 50°, then overnight for approximately 17 hours at room temperature. The reaction product was collected by filtration, washed with benzene and petroleum ether, and pumped dry for 4.5 hours in a 55°-60° vacuum overn, to yield the compound structurally depicted above as a solid, m.p. 110°-113° C.

Anal. Calc'd for $C_{18}H_{22}ClN_3O_4$: C, 56.92; H, 5.84; N, 11.06. Found: C, 55.73; H, 5.98; N, 10.37.

NMR ($CDCl_3$ and TMS): $\delta$=7.62(3H); 7.40(benzene, 5.3H); 7.01(3H); 5.95(2H); 3.95(3H); 3.40(3H); 3.07(2H); 1.50(6H).

EXAMPLE IV

The Preparation of the compound of the formula:

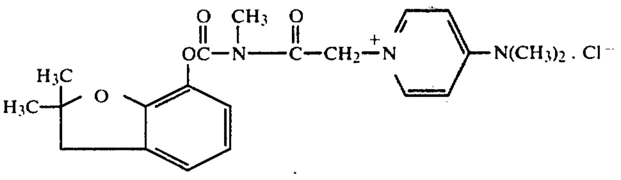

2,3-Dihydro-2,2-dimethyl-7-benzofuranyl N-chloroacetyl-N-methylcarbamate (3.0 g, 0.010 m) and 1.35 g of 4-N,N-dimethylaminopyridine (0.011 m) were stirred at 50° in 10 ml of benzene for one hour. The reaction product was collected by filtration, washed with benzene and petroleum ether, recrystallized from $CH_2Cl_2$ and benzene, washed with petroleum ether and dried at 55°-60° C. in a vacuum oven for 4.5 hours to yield the compound structurally depicted above as a solid, mp. 230°-231° C.

Anal: Calc'd for: $C_{21}H_{26}ClN_3O_4$: C, 60.07: H, 6.24: N, 10.01. Found: C, 58.35; H, 6.49; N, 8.91.

NMR ($CDCl_3$ and TMS): $\delta$=8.3-8.7(2H); 7.4 (benzene, 2.5H); 7.4-6.7(5H); 5.8(2H); 3.34(3H); 3.18(6H); 3.07(2H); 1.5(6H).

EXAMPLE V

The Preparation of a compound of the formula:

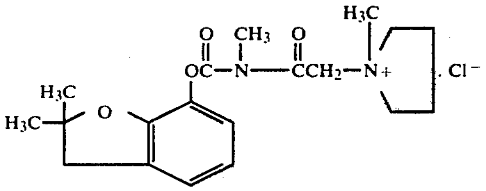

2,3-Dihydro-2,2-dimethyl-7-benzofuranyl N-chloroacetyl-N-methylcarbamate (3.0 g, 0.010 m) and N-methylpyrrolidine (1.0 g, 0.011 m) were stirred at 50° in benzene for 4 hours. The reaction product was collected by filtration, washed with benzene and petroleum ether and pumped on at 60° for 2 hours in a vacuum oven, to yield the compound structurally depicted above as a solid, mp. 147.148° C.

Anal. Calc. for $C_{19}H_{27}ClN_2O_4$: C, 59.60; H, 7.11; N, 7.32. Found: C, 58.48; H, 7.31; N, 6.64.

NMR ($CDCl_3$+TMS): $\delta$=7.3-6.7(3H); 5.50(2H); 4.00(4H); 3.37(6H); 3.03(2H); 2.87(0.8H); 2.13(4H); 1.47(6H).

EXAMPLE VI

The Preparation of a compound of the formula:

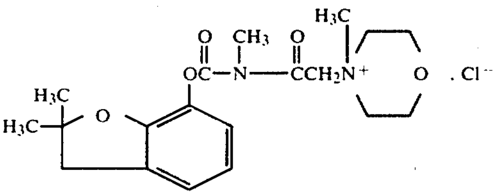

2,3-Dihydro-2,2-dimethyl-7-benzofuranyl N-chloroacetyl-N-methylcarbamate (3.0 g, 0.010 m) and 5.12 g N-methylmorpholine were stirred at 80° for 6 hours. The compound structurally depicted above was collected as a solid by filtration, mp 192°-195° C.

Anal. calc. for $C_{19}H_{27}N_2O_5Cl$: C, 57.21; H, 6.82; N, 7.02. Found: C, 56.75; H, 7.05; N, 4.85.

NMR($D_2O$ and TMS): $\delta$7.4-6.8(3H); 4.80(2H); 4.3-3.0(16H); 1.47(6H).

EXAMPLE VII

The Preparation of a compound of the formula:

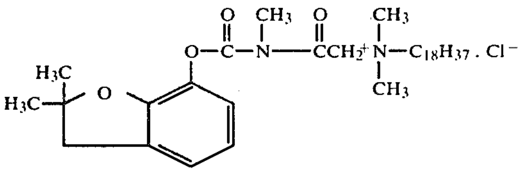

2,3-Dihydro-2,2-dimethyl-7-benzofuranyl N-chloroacetyl-N-methylcarbamate (3.00 g, 0.010 m) and N,N-dimethyloctadecylamine (3.60 g, 0.012 m were stirred at 45°-50° C. for 2¾ hours in 15 ml of benzene. The mixture was evaporated to yield 7.4 g of amber oil. Ethyl acetate was added, and insoluble solids were filtered. The filtrate was evaporated to yield the compound structurally depicted above as an oil.

Anal. Calc. for $C_{34}H_{59}N_2O_4Cl$: C, 68.60; H, 9.99 N, 4.70. Found: C, 67.46; H, 10.76; N, 4.50.

NMR ($CDCl_3$ and TMS): $\delta$=7.3-6.5 (3H); 5.32 (2H); 4.0-2.5 (12H); 1.5 and 1.27 (38H); 0.9 (3H).

EXAMPLE VIII

The Preparation of a compound of the formula:

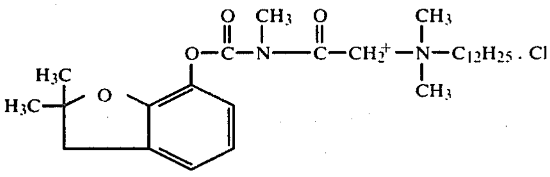

2,3-Dihydro-2,2-dimethyl-7-benzofuranyl N-chloroacetyl-N-methylcarbamate (3.0 g, 0.010 m,) and N,N-dimethyldodecylamine (2.29 g, 0.011 m) were stirred between 45° and 50° for 3 hours. The reaction mixture was evaporated to yield 5.3 g of the compound structurally depicted above as an oil.

Anal. Calc. for $C_{28}H_{47}N_2O_4Cl$: C, 65.80; H, 9.27; N, 5.48. Found: C, 63.17; H, 9.66; N, 5.20.

NMR ($CDCl_3$ and TMS): $\delta$=7.2-6.6(3H); 5.3(1.4H) 3.9-2.6 (several broad absorbances, 13H); 1.6-0.7(3 broad asborbances, 35H).

EXAMPLE IX

The preparation of a Compound of the formula:

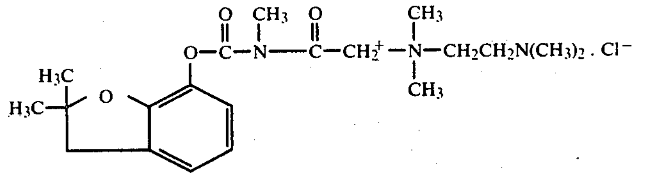

2,3-Dihydro-2,2-dimethyl-7-benzofuranyl N-chloroacetyl-N-methylcarbamate (3.0 g, 0.010 m) and 1.29 g (0.011 m) of N,N,N', N'-tetramethylethylenediamine were stirred in 25 ml of benzene for one hour at 40° C., for 16½ hours at room temperature (~25° C.) and for 3 hours at 45°-50° C. After an additional hour at room temperature, structure was confirmed by nuclear magnetic resonance spectroscopy (NMR) in $CDCl_3$ with TMS.

EXAMPLE X

The Preparation of a compound of the formula:

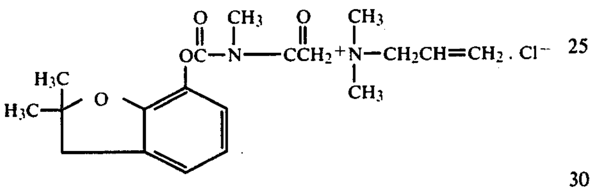

2,3-Dihydro-2,2-dimethyl-7-benzofuranyl N-chloroacetyl-N-methylcarbamate (3.0 g, 0.010 m) and N,N-dimethylallylamine (1.0 g), were stirred in 15 ml of benzene for five hours at 50°-55° C. An additional 3.33 g of N,N-dimethylallylamine was added and the mixture was stirred overnight then filtered. Solids were washed with benzene and hexane than pumped at 1 mm at 60° C. to yield 2.50 g of the compound structurally depicted above as a solid whose structure was confirmed by nuclear magnetic resonance spectroscopy (NMR).

NMR ($CDCl_3$+TMS) $\delta$=7.3-6.6(3.1 H); 6.1-5.5 (3.6 H); 5.36 (broad, 1.8 H); 4.8-4.4 (2.2 H); 3.57 (broad, 6.2 H);

3.39 (broad, ~3 H); 3.33 (~1.3 H; impurity); 3.1 H (broad, 2.0 H); 2.3 H (impurity, ~0.9 H); 1.49 (broad, 6.0 H).

EXAMPLE XI

The Preparation of a compound of the formula:

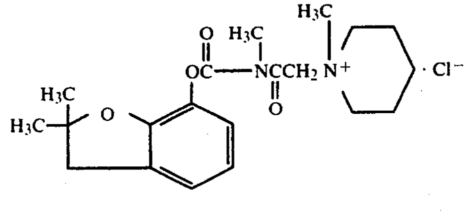

2,3-Dihydro-2,2-dimethyl-7-benzofuranyl N-chloroacetyl-N-methylcarbamate (3.0 g, 0.010 m) and 1.10 g (0.011 m) of N-methylpiperidine were stirred in 10 ml of benzene from 45°-50° C., for 2 hours, at room temperature overnight (~17 hrs.) then at 45°-50° C. for 3 hours to produce the compound structurally depicted above. Structure was confirmed by nuclear magnetic resonance spectroscopy (NMR).

Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of test compound. The test concentrations in parts per million by weight employed in the tests described hereinbelow were obtained by appropriate dilutions of the stock suspension with water. The test procedures were as follows:

BEAN APHID FOLIAGE SPRAY TEST

Adults and nymphal stages of the bean aphid (*Aphis fabae Scop.*) reared on potted dwarf nasturtium plants at 65°-70° F. and 50-70 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being uprighted were considered dead. Aphids remaining on the plants were observed closely for movement and those which were unable to move the length of the body upon stimulator by prodding were considered dead. Percent mortality was recorded for various concentration levels.

SOUTHERN ARMYWORM LEAF SPRAY TEST

Larvae of the southern armyworm (*Prodenia Eridania,* (Cram.), reared on Tendergreen bean plants at a temperature of 80°±5° F. and relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig. air pressure.

This application which lasted 25 seconds was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

MEXICAN BEAN BEETLE LEAF SPRAY TEST

Fourth instar larvae of the Mexican bean beetle (*Epilachna varivestis,* Muls.) reared on Tendergreen bean plants at a temperature of 80°±5° and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

FLY BAIT TEST

Four to six day old adult house flies (*Musca domestica,* L.) reared according to the specifications of the Chemical Specialties Manufacturing Association (Blue Book, McNair-Dorland Co., NY., 1954; pages 243–244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a one inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

MITE FOLIAGE SPRAY TEST

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two- and-a-half inch clay pot. 150–200 mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to give a suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted for 25 seconds was sufficient to wet the plants to run-off. As a control, 100–110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding, was considered living.

In these test the pesticidal activity of the compounds against aphid, mite, Southern Armyworm, Mexican Bean Beetle, and house fly was rated as follows:

A=Excellent control
B=Partial control
C=No control

PHYTOTOXICITY TEST

Experiments were also conducted to determine the phytotoxicity of representative compositions with respect to healthy fresh plants. Solutions of the compounds were prepared as described above to provide a concentration of 2500 parts per million of the test compound. The test plants were sprayed in accordance with the procedure described above for the Mite Foliage Spray Test so as to deliver approximately 100 milliliters of test solution to the leaves of each plant tested. The sprayed plants and controls were set aside for approximately one hour to allow the solutions to dry and were then placed in the greenhouse. After ten days the plants were visually inspected to determine the extent of foliage injury. A rating of 1 indicates no perceptible injury; 5 indicates the plant was dead and ratings of 2, 3 and 4 indicate intermediate degrees of injury based upon the number and extent to which leaves were injured.

The results of these experiments are summarized and set forth in Table I below.

TABLE I

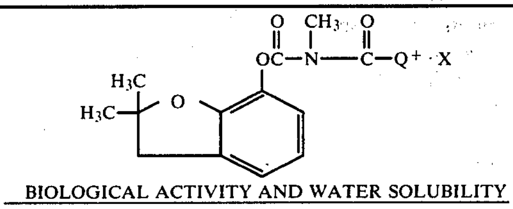

BIOLOGICAL ACTIVITY AND WATER SOLUBILITY

| | | BIOLOGICAL ACTIVITY | | | | | | | | | |
|---|---|---|---|---|---|---|---|---|---|---|---|
| | | Pesticidal | | | | | | | | | |
| | % Water | | | | Mexican | | POST-Emergent Herbicidal | | | | |
| Q+X | Solubility, 25° C. | Aphid | Mite | Southern Armyworm | Bean Beetle | Fly | Bean | Corn | Tomato | Cotton | Soy bean |
| $-H_2C-\overset{+}{N}(CH_3)_3 \cdot Cl^-$ | 57 | A | C | A | A | A | 1 | 1 | 2 | 2 | 2 |
| 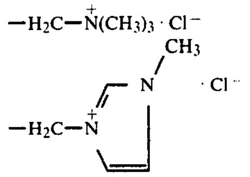 | 37 | A | A | A | A | A | 2 | 1 | 1 | 1 | 2 |
| 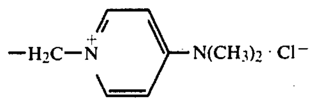 | 16 | A | A | A | A | A | 2 | 1 | 1 | 1 | 2 |
| 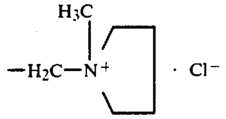 | 49 | A | A | A | A | A | 2 | 1 | 1 | 2 | 2 |
| 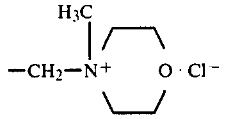 | 14 | A | B | A | A | A | — | — | — | — | — |
| 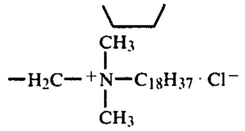 | Soluble, (>25%) | B | C | A | A | A | 2 | 2 | 1 | 2 | 2 |
| 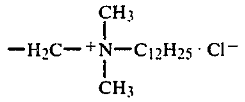 | Soluble, (>25%) | A | A | A | A | A | 2 | 2 | 2 | 2 | 2 |

The data in TABLE I clearly illustrates the broad spectrum high level pesticidal activity and the significant water solubility exhibited by the compounds of this invention. In addition, the data shows the low levels of phytotoxicity exhibited by the compounds of this invention. It should be understood that the pests evaluated are representative of a wider variety of pest which can be controlled by the compounds of this invention.

The compounds contemplated in this invention may be applied as insecticides, nematocides and miticides according to methods known to those skilled in the art. Pesticidal compositions usually comprise a carrier and/or diluent, either liquid or solid. Suitable liquid diluents or carriers include water, petroleum distillates or other liquid carriers with or without surface active agents. Useful solid carriers include clay, talc, bentonite, diatomaceous earth, fullers earth and the like.

Pesticidal compositions containing the compounds of this invention as the active toxicant may be used in the form of liquid concentrates or as powder, granular formulations, or other solid formulations. However, because of the unique water solubility characteristics of many of the compounds of this invention, either the technical materials or any appropriate formulation may be dissolved directly in water in sufficient amounts to attain the desired concentration levels. The water solution may then be applied to the pest by any conventional method known to those skilled in the art.

The required amount of the toxicants contemplated herein may be applied per acre treated in from 1 to 200 gallons or more of liquid carrier and/or diluent or in from about 5 to 500 pounds of inert solid carrier and/or diluent. The concentration in solid formulations may vary from about 0.5 to about 100 percent by weight. Satisfactory sprays, dusts, or granules for general use contain from about ¼ to 15 pound of active toxicant per acre.

The pesticides contemplated herein prevent attack by insects and mites upon plants or other material to which the pesticides are applied, and they have relatively high residual toxicity coupled with reduce levels of peroral mammalian toxicity. With respect to plants, they have a high margin of safety in that when used in sufficient amount to kill or repel the insects, they do not burn or injure the plant, and they resist weathering which includes decomposition by ultra-violet light, oxidation, or hydrolysis in the presence of moisture or, at least such decomposition, oxidation and hydrolysis as would materially decrease the desirable pesticidal characteristic of the toxicants or impart undesirable characteristics, for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. Mixtures of the active compound of this invention may be employed as well as combinations of the active compounds of this invention with other biologically active compounds.

What is claimed is:

1. A compound of the formula:

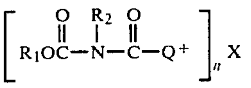

wherein:

n is 1, 2 or 3;

$R_1$ is benzofuranyl, benzodioxanyl benzothienyl, dihydrobenzothienyl, benzodioxolanyl or dihydrobenzofuranyl all of which may be either unsubstituted or substituted with one or more alkyl groups having from 1 to 8 carbon atoms;

$R_2$ is alkyl having from 1 to 8 carbon atoms;

X is a quaternising anion selected from the group consisting of mono-valent, divalent or trivalent inorganic or organic anions whose charge equals n;

$Q^+$ is an organic radical of the formula:

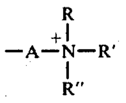

wherein:

A is a divalent aliphatic hydrocarbon radical having from 1 to 25 carbon atoms;

R, R' and R'' are (a) individually, either substituted or unsubstituted alkyl, alkoxyalkyl, alkenyl or alkynyl; or (b) when R and R' are the same or different and are methyl or ethyl, R'' is either a substituted or unsubstituted phenyl, naphthyl, cycloalkyl, cycloalkenyl or a 5 or 6 membered heterocyclic ring structure which includes carbon and one or two heteroatoms of oxygen or nitrogen or a combination of oxygen and nitrogen; or (c) when R is alkyl of from 1 to 4 carbon atoms, R' and R'' together may form either a substituted or unsubstituted alkenylene or alkylene chain having from 2 to 20 carbon atoms which completes a 3, 4, 5, 6, 7, 8 or 9 membered monocyclic ring structure; said chain may include one or two heteroatoms of oxygen or nitrogen or a combination of oxygen and nitrogen; or (d) R, R' and R'' together may form a substituted or an unsubstituted alkylene or alkenylene chain having from 2 to 20 carbon atoms which completes a 3, 4, 5, 6, 7, 8, or 9 membered monocyclic or bicyclic ring structure, and said chain may include one or two heteroatoms of oxygen or nitrogen or a combination of oxygen and nitrogen;

wherein the permissible substituents that may be substituted on R, R' and R'' are one or more alkoxy, alkyl alkanoyloxy, alkoxycarbonyl, cyano, halo, nitro, dialkylamino or alkanoyl groups; with the proviso that the sum of aliphatic carbon atoms included in R, R' and R'' may not be more than thirty-five.

2. A compound according to claim 1 wherein A is a linear or branched alkylene or alkenylene chain having from 1 to 25 carbon atoms.

3. A compound according to claim 1 wherein:

R, R' and R'' are the same or different and are alkyl, alkoxyalkyl, alkenyl or alkynyl all of which may be either unsubstituted or substituted with one or more alkanoyloxy, alkoxy, alkoxycarbonyl, alkanoyl or dialkylamino groups.

4. A compound according to claim 1 wherein:

R and R' are the same or different and are methyl or ethyl; and R'' is substituted or unsubstituted phenyl, naphthyl, cycloalkyl, cycloalkenyl or a 5 to 6 membered ring structure which may include carbon and one or two heteroatoms of oxygen and/or nitrogen in any combination, wherein the permissible substituents are one or more alkoxy, alkyl alkanoyloxy, alkoxycarbonyl, alkanoyl or dialkylamino groups.

5. A compound according to claim 1 wherein:

R, R' and R'' together form a substituted or unsubstituted alkylene or alkenylene chain which completes a 3, 4, 5, 6, 7, 8 or 9 membered monocyclic or bicyclic ring structure, said chain may include one or two heteroatoms of oxygen or nitrogen or a combination of oxygen and nitrogen wherein the permissible substituents are one or more alkoxy, alkyl alkanoyloxy, alkoxycarbonyl, alkanoyl or dialkylamino groups.

6. A compound according to claim 1 wherein:

R is alkyl having from 1 to 4 carbon atoms;

R' and R'' together form either a substituted or unsubstituted alkenylene or alkylene chain having from 2 to 20 carbon atoms which completes a 3, 4, 5, 6, 7, 8 or 9 membered monocyclic ring structure, said chain may include one or two heteroatoms of oxygen or nitrogen or a combination of oxygen and nitrogen wherein the permissible substituents are one or more alkyl, alkoxy, alkanoyloxy, alkoxycarbonyl, alkanoyl or dialkylamino groups.

7. A compound according to claim 1 wherein X is chloride, bromide, fluoride, nitrate, iodide, bicarbonate, carbonate, sulfate, phosphate, acetate, propionate, lactate, formate, succinate, maleate, tartrate, citrate, p-toluenesulfonate, benzenesulfonate or methanesulfonate.

8. Compound according to claim 1 wherein X is chloride.

9. A compound according to claim 1 wherein $R_1$ is benzodioxolanyl or dihydrobenzofuranyl either unsubstituted or substituted with one or more alkyl groups.

10. A compound according to claim 1 wherein $R_1$ is 2,3-dihydro-2,2-dimethyl-7-benzofuranyl.

11. A compound according to claim 1 wherein $R_1$ is 2,2-dimethyl-4-benzo-1,3-dioxolanyl.

12. A compound according to claim 1 wherein $R_2$ is methyl.

13. A compound of the formula:

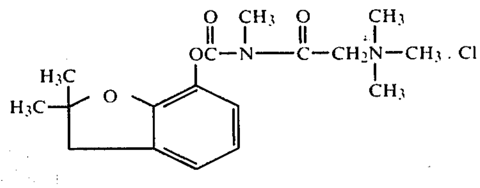

14. A compound of the formula:

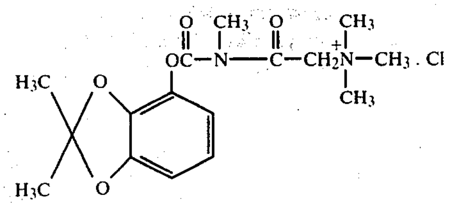

15. An insecticidal and miticidal composition comprising an acceptable carrier and as the active toxicant an insecticidally or miticidally effective amount of a compound according to claim 1.

16. An insecticidal and miticidal composition comprising an acceptable carrier and as the active toxicant an insecticidally or miticidally effective amount of a compound according to claim 2.

17. An insecticidal and miticidal composition comprising an acceptable carrier and as the active toxicant an insecticidally or miticidally effective amount of a compound according to claim 3.

18. An insecticidal and miticidal composition comprising an acceptable carrier and as the active toxicant an insecticidally or miticidally effective amount of a compound according to claim 4.

19. An insecticidal and miticidal composition comprising an acceptable carrier and as the active toxicant an insecticidally or miticidally effective amount of a compound according to claim 5.

20. An insecticidal and miticidal composition comprising an acceptable carrier and as the active toxicant an insecticidally or miticidally effective amount of a compound according to claim 6.

21. An insecticidal and miticidal composition comprising an acceptable carrier and as the active toxicant an insecticidally or miticidally effective amount of a compound according to claim 7.

22. An insecticidal and miticidal composition comprising an acceptable carrier and as the active toxicant an insecticidally or miticidally effective amount of a compound according to claim 8.

23. An insecticidal and miticidal composition comprising an acceptable carrier and as the active toxicant an insecticidally or miticidally effective amount of a compound according to claim 9.

24. An insecticidal and miticidal composition comprising an acceptable carrier and as the active toxicant an insecticidally or miticidally effective amount of a compound according to claim 10.

25. An insecticidal and miticidal composition comprising an acceptable carrier and as the active toxicant an insecticidally or miticidally effective amount of a compound according to claim 11.

26. An insecticidal and miticidal composition comprising an acceptable carrier and as the active toxicant an insecticidally or miticidally effective amount of a compound according to claim 12.

27. An insecticidal and miticidal composition comprising an acceptable carrier and as the active toxicant an insecticidally or miticidally effective amount of a compound according to claim 13.

28. An insecticidal and miticidal composition comprising an acceptable carrier and as the active toxicant an insecticidally or miticidally effective amount of a compound according to claim 14.

29. A method of controlling insects and mites which comprises subjecting them to an insecticidally or miticidally effective amount of a compound according to claim 1.

30. A method of controlling insects and mites which comprises subjecting them to an insecticidally or miticidally effective amount of a compound according to claim 2.

31. A method of controlling insects and mites which comprises subjecting them to an insecticidally or miticidally effective amount of a compound according to claim 3.

32. A method of controlling insects and mites which comprises subjecting them to an insecticidally or miticidally effective amount of a compound according to claim 4.

33. A method of controlling insects and mites which comprises subjecting them to an insecticidally or miticidally effective amount of a compound according to claim 5.

34. A method of controlling insects and mites which comprises subjecting them to an insecticidally or miticidally effective amount of a compound according to claim 6.

35. A method of controlling insects and mites which comprises subjecting them to an insecticidally or miticidally effective amount of a compound according to claim 7.

36. A method of controlling insects and mites which comprises subjecting them to an insecticidally or miticidally effective amount of a compound according to claim 8.

37. A method of controlling insects and mites which comprises subjecting them to an insecticidally or miticidally effective amount of a compound according to claim 9.

38. A method of controlling insects and mites which comprises subjecting them to an insecticidally or miticidally effective amount of a compound according to claim 10.

39. A method of controlling insects and mites which comprises subjecting them to an insecticidally or miticidally effective amount of a compound according to claim 11.

40. A method of controlling insects and mites which comprises subjecting them to an insecticidally or miticidally effective amount of a compound according to claim 12.

41. A method of controlling insects and mites which comprises subjecting them to an insecticidally or miticidally effective amount of a compound according to claim 13.

42. A method of controlling insects and mites which comprises subjecting them to an insecticidally or miticidally effective amount of a compound according to claim 14.

43. A compound of the formula:

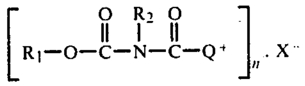

wherein:

n is 1, 2 or 3;

$R_1$ is dihydrobenzofuranyl, either unsubstituted or substituted with one or more alkyl groups;

$R_2$ is alkyl having from 1 to 8 carbon atoms;

X is chloride, bromide, fluoride, nitrate, iodide, bicarbonate, carbonate, sulfate, phosphate, acetate, propionate, lactate, formate, succinate, maleate, tartrate, citrate, arenesulfonates, or alkanesulfonates, $Q^+$ is an organic radical of the formula"

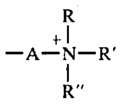

wherein:

A is a divalent aliphatic hydrocarbon having from 1 to 25 carbon atoms;

R, R' and R" are (a) individually, either substituted or unsubstituted alkyl, alkoxyalkyl, alkenyl or alkynyl; or (b) when R and R' are the same or different and are methyl or ethyl, R" is either substituted or unsubstituted phenyl, naphthyl, cycloalkyl, cycloalkenyl or a 5 or 6 membered ring structure which may include carbon and one or two heteroatoms of oxygen or nitrogen, or a combination of oxygen and nitrogen; or (c) when R is alkyl of from 1 to 4 carbon atoms, R' and R" together may form either a substituted or unsubstituted alkenylene or alkylene chain which completes a 3, 4, 5, 6, 7, 8 or 9 membered monocyclic ring structure which may include one or two heteroatoms of oxygen or nitrogen or a combination of oxygen and nitrogen; or (d) R, R' and R" together form a substituted or unsubstituted alkenylene or alkylene chain which completes a 3, 4, 5, 6, 7, 8 or 9 membered monocyclic or bicyclic ring structure which may include one or two heteroatoms of oxygen or nitrogen or a combination of oxygen and nitrogen;

wherein the permissible substituents that may be substituted on R, R' and R" are one or more alkoxy, alkyl alkanoyloxy, alkoxycarbonyl, cyano, halo, nitro, dialkylamino or alkanoyl groups;

with the proviso that the sum of aliphatic atoms included in R, R' and R" may not be more than thirty-five.

44. An insecticidal miticidal composition comprising an acceptable carrier and as the active toxicant an insecticidally or miticidally effective amount of a compound according to claim 43.

45. A method of controlling insects and mites which comprises subjecting them to an insecticidally or miticidally effective amount of a compound according to claim 43.

46. A compound according to claim 43 wherein: R, R' and R" are:

(a) individually, either substituted or unsubstituted alkyl, alkoxyalkyl, alkenyl or alkynyl; or (b) when R and R' are the same or different and are methyl or ethyl, R" is either a substituted or unsubstituted phenyl, naphthyl cycloalkyl, cycloalkenyl or a 5 or 6 membered ring structure which may include carbon and one or two heteroatoms of oxygen or nitrogen or a combination of oxygen and nitrogen.

47. A compound according to claim 46 wherein A is a linear or branched alkylene or alkenylene chain having from 1 to 25 carbon atoms.

48. A compound of the formula:

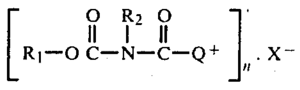

wherein:

n is 1, 2 or 3;

$R_1$ is dihydrobenzofuranyl, either substituted or unsubstituted with one or more alkyl groups;

X is a quaternising anion selected from the group consisting of mono-valent, divalent or trivalent inorganic or organic anion whose charge equals n;

$Q^+$ is an organic radical of the formula:

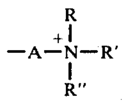

wherein:

A is a divalent alkylene or alkenylene radical having from 1 to 25 carbon atoms;

R, R' and R" are:

(a) individually, either substituted or unsubstituted alkyl, alkoxyalkyl, alkenyl or alkynyl group;

(b) when R, R' are the same or different and are methyl or ethyl, R" is either substituted or unsubstituted phenyl, naphthyl, cycloalkyl, cycloalkenyl or a 5 or 6 membered heterocyclic ring structure which includes carbon and one or two heteroatoms of oxygen or nitrogen or a combination of oxygen and nitrogen;

wherein the permissible substituents are one or more alkoxy, alkyl, alkanoyloxy, alkoxycarbonyl, cyano, halo, nitro, dialkylamino or alkanoyl groups;

With the proviso that the sum of aliphatic carbon atoms included in R, R' and R" may not be more than thirty-five.

* * * * *